United States Patent
Kaye et al.

(10) Patent No.: US 7,218,395 B2
(45) Date of Patent: May 15, 2007

(54) RAPID PHARMACEUTICAL IDENTIFICATION AND VERIFICATION SYSTEM

(75) Inventors: Stephen T. Kaye, Raleigh, NC (US);
Prasant Potuluri, Raleigh, NC (US);
David J. Brady, Durham, NC (US);
Michael Fuller, Chapel Hill, NC (US);
Michael E. Sullivan, Raleigh, NC (US)

(73) Assignee: Optopo Inc., Morrisville, NC (US)

( * ) Notice: Subject to any disclaimer, the term of this patent is extended or adjusted under 35 U.S.C. 154(b) by 0 days.

(21) Appl. No.: 11/454,923

(22) Filed: Jun. 19, 2006

(65) Prior Publication Data

US 2007/0008523 A1    Jan. 11, 2007

Related U.S. Application Data (63) Continuation-in-part of application No. 10/417,066, filed on Apr. 16, 2003, now Pat. No. 7,092,101, which is a continuation-in-part of application No. 11/334,546, filed on Jan. 19, 2006.

(60) Provisional application No. 60/811,101, filed on Jun. 6, 2006, provisional application No. 60/725,311, filed on Oct. 12, 2005, provisional application No. 60/705,173, filed on Aug. 4, 2005, provisional application No. 60/644,522, filed on Jan. 19, 2005.

(51) Int. Cl.
*G01J 3/44* (2006.01)
*G01N 21/65* (2006.01)

(52) U.S. Cl. ...................... 356/301; 356/328
(58) Field of Classification Search ............... 356/301, 356/326, 328
See application file for complete search history.

(56) References Cited

U.S. PATENT DOCUMENTS

| | | | |
|---|---|---|---|
| 5,386,287 A * | 1/1995 | Berssen et al. | 356/326 |
| 5,504,332 A | 4/1996 | Richmond | |
| 5,700,998 A | 12/1997 | Palti | |
| 5,760,399 A | 6/1998 | Trygstad | |
| 5,845,264 A | 12/1998 | Nellhaus | |
| 5,859,703 A * | 1/1999 | Aldridge et al. | 356/319 |
| 6,075,594 A | 6/2000 | Thomas | |
| 6,111,639 A | 8/2000 | Reduto | |
| 6,317,648 B1 * | 11/2001 | Sleep et al. | 700/216 |
| 6,505,461 B1 | 1/2003 | Yasunaga | |
| 6,543,692 B1 | 4/2003 | Nellhaus | |
| 6,771,369 B2 | 8/2004 | Rzasa | |
| 6,776,341 B1 | 8/2004 | Sullivan | |
| 6,799,725 B1 | 10/2004 | Hess | |
| 7,006,214 B2 | 2/2006 | Rzasa | |
| 2004/0057040 A1 | 3/2004 | Beckenkamp | |

FOREIGN PATENT DOCUMENTS

| | | |
|---|---|---|
| JP | 9-16681 | 6/1995 |
| JP | 10-33638 | 10/1998 |

* cited by examiner

*Primary Examiner*—F. L. Evans
(74) *Attorney, Agent, or Firm*—Kasha Law PLLC; John R. Kasha (57) ABSTRACT

A prescription verification system includes a database that contains a plurality of spectral signatures corresponding to identified pharmaceuticals. A multimodal multiplex sampling (MMS) spectrometer obtains a spectra of a pharmaceutical to be identified and verified. The pharmaceutical can be inside or out of a vial. The prescription verification system includes algorithms for matching spectra of pharmaceuticals to be verified obtaining using the MMS spectrometer to spectral signatures contained in the database corresponding to identified pharmaceuticals. The prescription verification system further includes algorithms for identifying such pharmaceuticals to be verified.

29 Claims, 8 Drawing Sheets

RAPID PHARMACEUTICAL IDENTIFICATION AND VERIFICATION SYSTEM

This application is a continuation-in-part application of U.S. patent application Ser. No. 10/417,066, filed Apr. 16, 2003 now U.S. Pat. No. 7,092,101, and a continuation-in-part application of U.S. patent application Ser. No. 11/334, 546, filed Jan. 19, 2006, which claims the benefit of U.S. Provisional Patent Application No. 60/644,522, filed Jan. 19, 2005 and U.S. Provisional Patent Application No. 60/705, 173, filed Aug. 4, 2005. This application also claims the benefit of U.S. Provisional Patent Application No. 60/725, 311, filed Oct. 12, 2005, and U.S. Provisional Patent Application No. 60/811,101, filed Jun. 6, 2006. All of the above mentioned applications are incorporated by reference herein in their entireties.

This invention was made with Government support under R44 RR023 907 awarded by the National Institutes of Health. The Government has certain rights in the invention.

BACKGROUND OF THE INVENTION

1. Field of the Invention

Embodiments of the present invention relates to systems and methods for the rapid identification and/or verification of pharmaceuticals using spectroscopic techniques. More particularly, some embodiments of the present invention relate to analyzing filled prescriptions using Raman Spectroscopy through closed bottles.

2. Background Information

Most states in the U.S. require that a registered pharmacist confirm whether a pharmaceutical delivered to a customer is indeed the pharmaceutical prescribed by the physician. Typically, such confirmation is accomplished by the pharmacist visually inspecting the dispensed pharmaceutical to verify its correctness. In fact, pharmacists can spend as much as 50% of their time visually verifying prescriptions.

Despite such pharmacist verification, errors are not uncommon, especially during peak operating hours. For example, according to the National Association of Boards of Pharmacy, as many as 5% of the 3 billion prescriptions filled each year are incorrect. These erroneous prescriptions are responsible for as many as 7,000 deaths annually in the United States. Further, due to a steadily decreasing number of pharmacists, and an expected increase in the annual demand for prescriptions to nearly 5 billion, the number of instances in which a customer receives the wrong prescription is anticipated to increase.

Not surprisingly, increasing prescription errors have resulted in a growing collection of consumer complaints about potentially serious errors such as wrong counts, wrong drugs and/or wrong dosages. Accompanying the increase in complaints are dramatically increased litigation costs associated with errors filling prescriptions. Thus, there is a strong need for a system to replace the present manual verification technique and allow the verification and validation steps to be performed automatically and more reliably. A by-product of such an automatic verification system is freeing up pharmacists' time so they can provide better service to their customers.

Several conventional automatic prescription verification techniques have been developed to address the problems with manual prescription verification. For example, conventional automatic visual verification techniques rely on comparing an electronic image of the prescribed medication, i.e., a picture of the prescribed medication retrieved from a data library, to the actual medication that is to be dispensed to a customer. However, conventional automatic visual identification methods rely on the incorrect assumption that all pharmaceuticals are visually distinct. Not only aren't all pharmaceuticals visually distinct, but the differences between even visually distinct pharmaceuticals may be so subtle that errors are likely occur. Finally, because automatic visual verification systems are somewhat duplicative of the manual visual verification technique described above, such systems are susceptible to the same drawbacks of manual verification systems, particularly the possibility of human error.

Spectroscopic analysis is a more reliable method of validating dispensed pharmaceuticals than using visual techniques. Spectroscopic techniques rely on a unique spectral signature exhibited by each pharmaceutical such as a pill, tablet, capsule, gelcap, gel and liquid. Accepted spectroscopic techniques for pharmaceutical verification include Near-Infrared (NIR) spectroscopy, UV and visible spectroscopy, Raman spectroscopy and Fourier Transform Infrared (FT-IR) spectroscopy.

For example, U.S. Pat. No. 6,771,369 to David Rzasa et. al. (the "Rzasa patent") discloses a specific method for pharmaceutical verification based on NIR spectroscopy for pharmacy validation and inspection. The Rzasa patent discloses a system in which the pharmacist opens the cap of the prescription vial or bottle containing the pharmaceuticals and places the vial or bottle under a NIR spectrometer. The system then obtains an NIR spectroscopic signature of the prescription and compares that signature to a database of signatures corresponding to known pharmaceuticals. The system verifies the prescription if the measured signature matches the signature in the database corresponding to the prescribed pharmaceutical.

However, the system described in the Rzasa patent suffers from several important drawbacks, including requiring the vial to be opened (and thus exposing the medicine to contamination), requiring roughly the same amount of time as with a visual inspection, and providing no chain of custody between the customer and the verified prescription, and thus no audit trail for forensic purposes. Furthermore, the NIR system described in the Rasza patent requires long integration times and lacks sufficient spectral contrast to uniquely, rapidly and repeatably identify a large number of pharmaceuticals accurately.

SUMMARY OF THE INVENTION

As described below, an embodiment of the present invention the present invention is a fully automated pharmaceutical identification and verification system that operates through a standard prescription vial or bottle without requiring cap removal/replacement, while providing superior speed of identification, and higher identification accuracy and repeatability. Furthermore, the invention provides a traceable chain of custody throughout the pharmaceutical verification process, as well as a means for establishing an audit trail for forensic purposes.

In a preferred embodiment of the present invention, Raman spectroscopy is used to identify the pharmaceutical. Preferably, the Raman spectrum is obtained through a closed prescription vial. A closed prescription vial is advantageous because it reduces the possibility of contamination as well as reduces the time necessary for identification. Once the pharmaceutical has been identified, the pharmacist, pharmacy technician and/or the system can verify that the prescription has been filled correctly. The present invention can also be carried out with pharmaceuticals in open vials, or even with loose pharmaceuticals. In a further preferred embodiment, the Raman spectroscopic method uses multimodal multiplex sampling spectroscopy for wide area collection of Raman photons scattered by the pharmaceutical under analysis.

In a typical use of an embodiment of the present invention, the prescription vial (or the loose pharmaceuticals) is (are) placed on a sensor bed. A laser diode is used to excite Raman-active modes in the pharmaceutical and to obtain a Raman spectral signature from the light scattered by the Raman modes in the pharmaceutical. For example, the laser diode may excite the Raman modes through the bottom, the sides or the top of a vial containing a pharmaceutical to be verified, or without passing through the vial if the vial is open or if the pharmaceuticals are loose. The Raman spectral signature obtained from the pharmaceutical is then compared to known Raman spectral signatures of pharmaceuticals stored in a database of known Raman spectra. The best match to one of the stored Raman spectral signatures in the database is displayed on a screen to be viewed by the pharmacist, the pharmacy technician and/or the customer. Optionally, the best match may be associated with a score, indicating the confidence level with which the recorded pharmaceutical Raman spectral signature matches the stored pharmaceutical signature. The pharmacist, the pharmacy technician, the customer and/or the system can then view the display to verify that the pharmaceutical identified by matching Raman spectral signatures corresponds to the prescribed pharmaceutical. For example, the system may read the bar code on the prescription vial identifying the prescription and compare that identification to the "best match" identification obtained from comparing the recorded Raman spectroscopic signature to the spectral signatures stored in the database.

In one embodiment, the present invention is a method for identifying and verifying a pharmaceutical in a prescription vial. The method includes storing a plurality of stored spectral signatures corresponding to known pharmaceuticals in a database and inserting the prescription vial containing the pharmaceutical whose identity is to be verified into a sample handling system. The method further includes measuring a spectral signature of the pharmaceutical whose identity is to be verified using a multimodal multiplex sampling (MMS) spectrometer and comparing the measured spectral signature to at least one of the stored spectral signatures. The method further includes determining if the measured spectral signature matches one of the stored spectral signatures, and if the measured spectral signature does not match one of the stored spectral signature, reporting that the identity of the pharmaceutical could not be determined, and if the measured spectral signature matches one of the stored spectral signatures, reporting the identity of the pharmaceutical.

In another embodiment, the present invention is a method for identifying pharmaceuticals in a closed vial. The method includes maintaining a database of known spectral signatures corresponding to known pharmaceuticals and placing the closed vial containing the pharmaceuticals in a spectrometer system. The method further includes directing a beam of electromagnetic radiation at the pharmaceuticals in the closed vial though the side, the bottom or the top of the closed vial and measuring a spectral signature from the electromagnetic radiation reflected, transmitted or scattered by the pharmaceuticals in the closed vial. The method further includes matching the measured spectral signature to one of the known spectral signatures, and reporting the identity of the pharmaceutical in the closed vial.

In another embodiment, the present invention is a method for identifying an unknown pharmaceutical in a prescription vial. The method includes creating, naming, and storing a plurality of known pharmaceutical spectral signatures using one or more multimodal multiplex sampling (MMS) spectrometers and measuring the spectral signature of an unknown pharmaceutical using a multimodal multiplex sampling (MMS) spectrometer. The method further includes comparing the measured spectral signature of the unknown pharmaceutical to at least one of the known spectral signatures and determining if the measured spectral signature of the unknown pharmaceutical matches one of the known spectral signatures. If the measured spectral signature of the unknown pharmaceutical does not match one of the known spectral signatures, a report or other indication is provided that the identity of the unknown pharmaceutical could not be determined. If, on the other hand, the measured spectral signature of the unknown pharmaceutical matches one of the known spectral signatures, a report or other indication of the identity of the unknown pharmaceutical is provided.

In another embodiment, the present invention is a prescription verification system. The system includes a database containing a plurality of spectral signatures corresponding to identified pharmaceuticals and a multimodal multiplex sampling (MMS) spectrometer. The system further includes algorithms for matching spectra of pharmaceuticals to be verified obtaining using the MMS spectrometer to spectral signatures contained in the database corresponding to identified pharmaceuticals and algorithms for identifying such pharmaceuticals to be verified.

DETAILED DESCRIPTION OF PREFERRED EMBODIMENTS OF THE INVENTION

Figure 1:
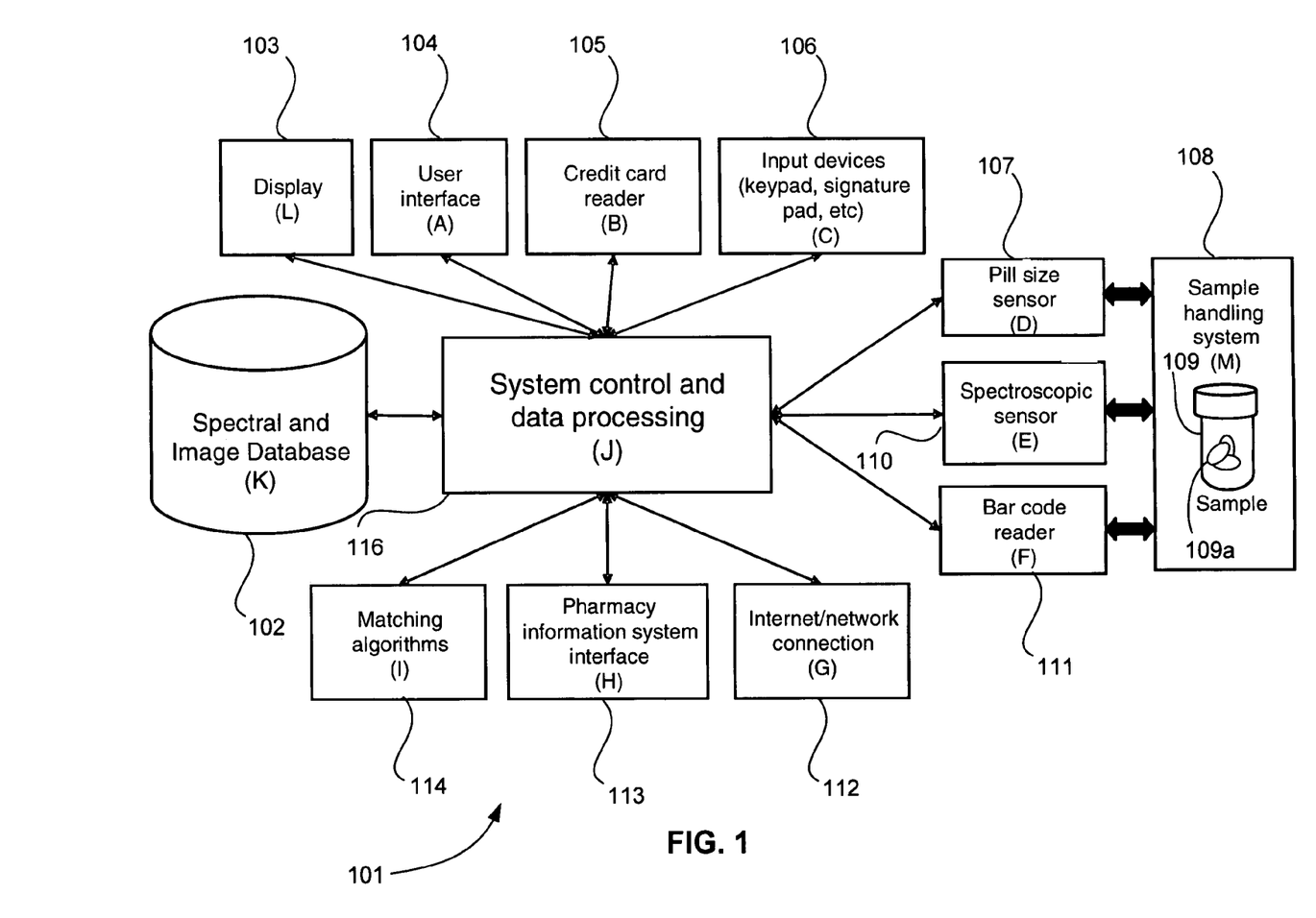
FIG. 1 is a schematic diagram of a pharmaceutical identification and verification system according to an embodiment of the present invention.

FIG. 1 is a schematic diagram of a system 101 for identifying and verifying pharmaceuticals according to an embodiment of the present invention. A standard prescription bottle or vial 109 containing one or more pharmaceuticals 109a, has been filled by a pharmacist, a pharmacy technician or an automated prescription dispensing unit. Vial 109 containing pharmaceuticals 109a is placed in a sample handling system 108. System 108 is in two-way communication with a spectroscopic sensor 110, such as a Raman sensor, a UV-VIS sensor, an FT-IR sensor, or an NIR sensor. Sample handling system 108 may optionally also be in two-way communication with imaging device 107 and a bar code reader 111. Imaging device 107, spectroscopic sensor 110 and bar code reader 111 are also in two-way communication with control and data processing system 116. Control and data processing system 116, in turn, is in two-way communication with spectral (and optionally image) database 102. One or more of display 103, user interface 104, credit card reader 105 and input devices 106 (e.g., a keyboard, a mouse, a signature pad or combinations of the preceding devices) are also in communication with control system 116.

Control system 116 contains matching algorithms 114 that may be used to match the measured spectral signature of the pharmaceutical whose identity is to be determined with one of the spectral signatures stored in database 102. A pharmacy information system interface 113 may be used to communicate with a pharmacy database. The pharmacy database can be used for example to check whether the prescribed pharmaceutical may have an adverse interaction with other pharmaceuticals being taken by the same patient, or to process insurance or credit card information. The pharmacy database can be a part of database 102, but is more generally a separate database. System 101 also includes an Internet/network connection 112 to provide any required connectivity and protocol support for communication over the Internet or other network.

Figure 2:
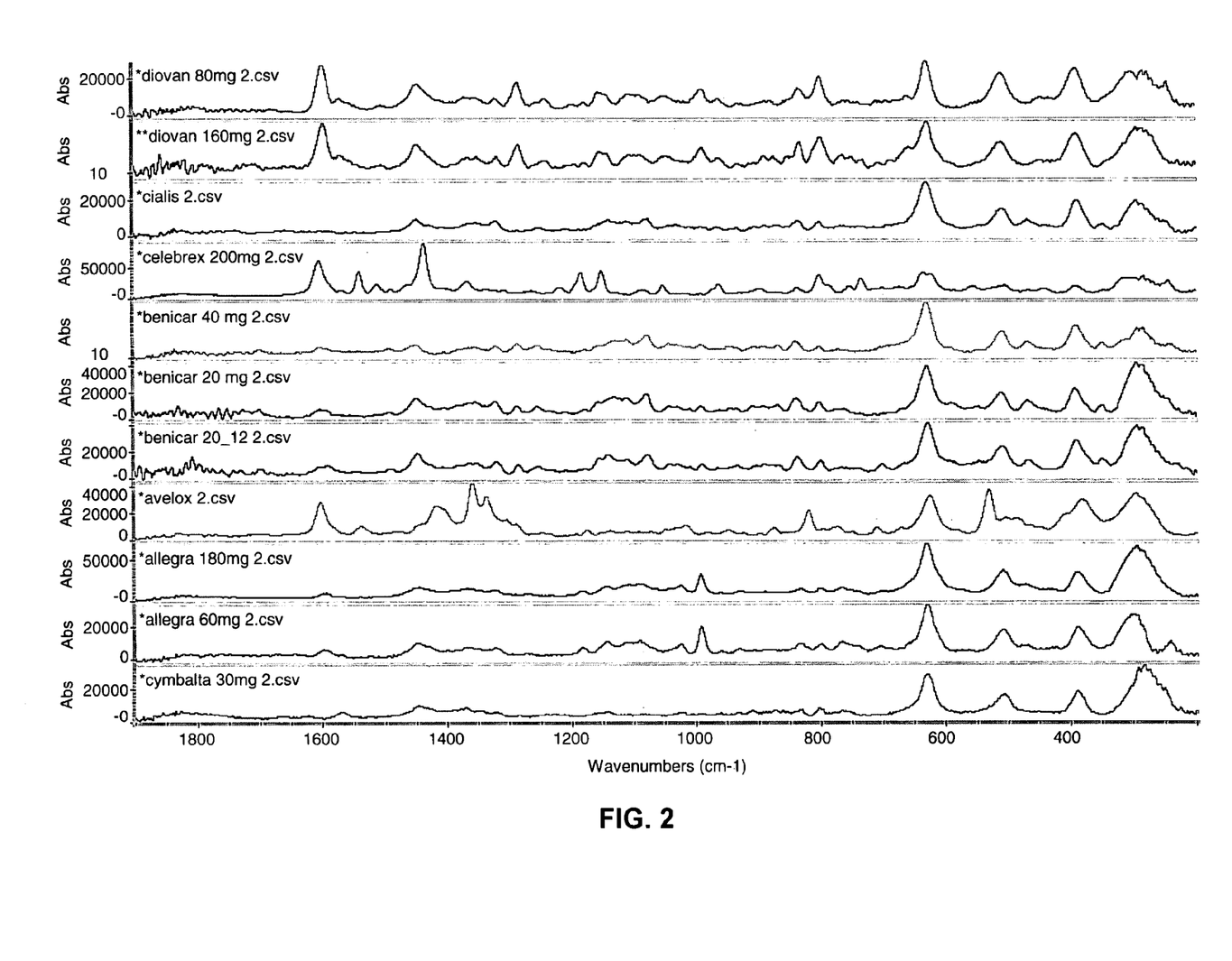
FIG. 2 shows exemplary Raman spectra of a number of common pharmaceuticals obtained through prescription vials.

FIG. 2 shows a series of Raman spectra of common pharmaceuticals (diovan 80 mg, diovan 160 mg, cialis, celebrex 200 mg, benicar 40 mg, benicar 20 mg, benicar 20-12, avelox, allegro 180 mg, allegro 60 mg and cymbalta 30 mg) obtained using an embodiment of the present invention. More specifically, these spectra were obtained by directing a laser diode beam through the bottom of respective prescription vials containing the pharmaceuticals. Similar spectra could have been obtained by directing the laser diode beam through the wall of the vial, or through the top, depending on the particular design of the system. Note that each of these pharmaceuticals has a completely unique spectral signature. The unique nature of the spectra provides a basis for distinguishing them from one another. Moreover, it can be seen that even different dosages of the same pharmaceutical exhibit unique spectra that can be distinguished from one other. Because the spectral signatures are unique, they can be used to identify the prescriptions. For example, in an embodiment of the invention, spectral (and imaging) database 102 (shown in FIG. 1) contains Raman spectra of all the tablets that could be dispensed by the pharmacy.

The spectra of a pharmaceutical being analyzed is compared to the spectra stored in database 102. If there is a match, the identity of the pharmaceutical corresponding to the spectrum matched in database 102 is selected as the identity of the pharmaceutical under analysis. Consequently, the spectra in database 102 serve as the reference for identifying pharmaceuticals. Preferably, database 102 is updated every time a new pharmaceutical is added to the pharmacy.

Figure 3:
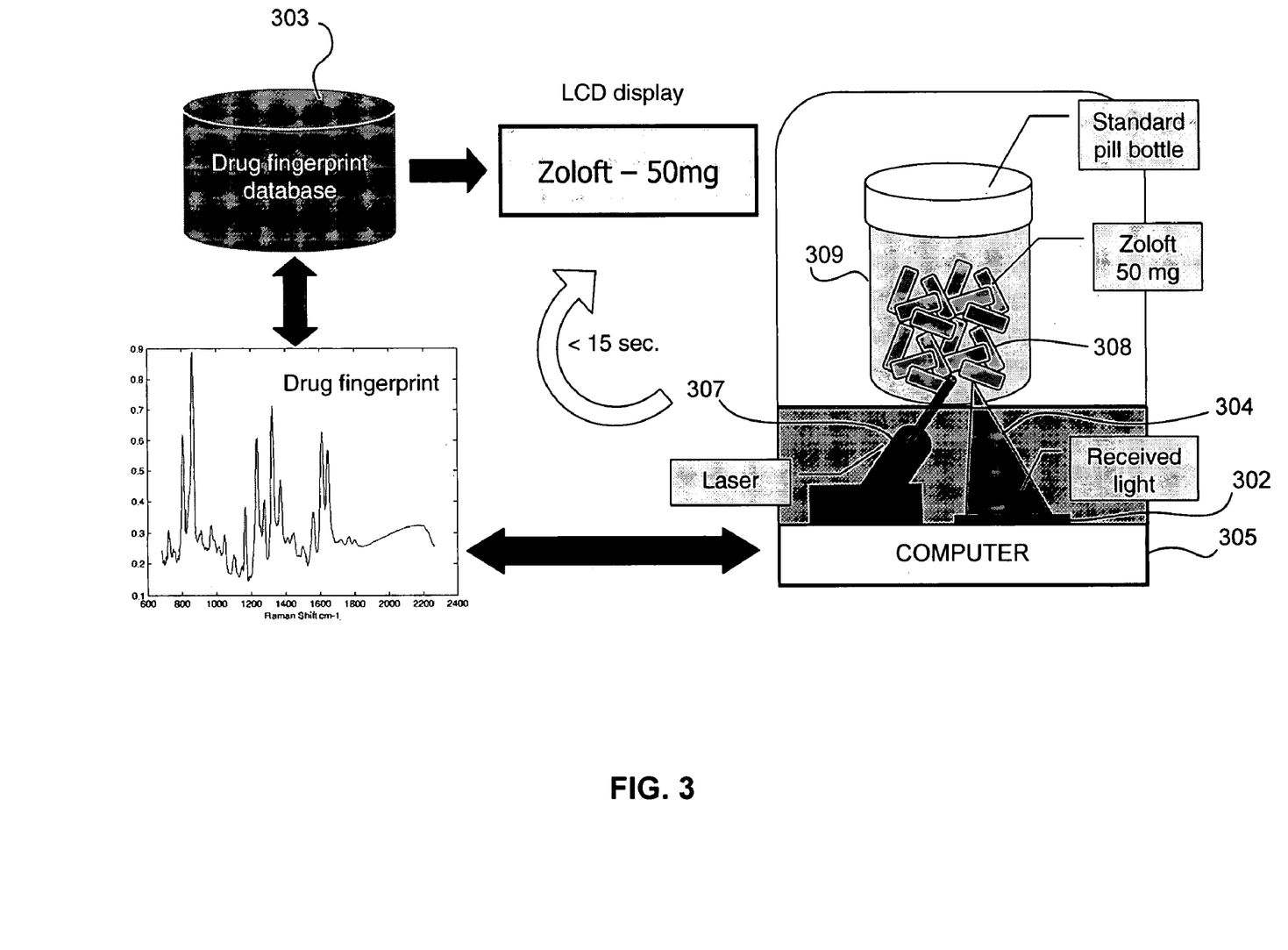
FIG. 3 illustrates is a schematic diagram of a multimodal spectroscopy engine for identifying and verifying a pharmaceutical according to an embodiment of the present invention.

FIG. 3 illustrates a multimodal multiplex sampling spectroscopy engine that can be used to obtain Raman spectra according to an embodiment of the present invention. As shown in FIG. 3, the Raman spectrometer uses a laser diode 307 to excite Raman-active modes in pharmaceuticals 308 through a closed prescription vial 309. The scattered Raman photons 304 are detected by detector 302, and sent to computer 305 for processing. The scattered Raman photons 304 exhibit vibration frequencies that are characteristic signatures of the tablet present in the vial. As shown by the examples illustrated in FIG. 2, each pharmaceutical exhibits a unique Raman spectrum. This is often referred to as a chemical signature or fingerprint of the pharmaceutical. Pharmaceuticals with varying dosage levels of the same active ingredient may have unique chemical signatures as well. Even slight variations in the active ingredients could produce a unique chemical signature. Therefore an analysis of the scattered Raman spectrum is indicative of the pharmaceutical and may also be indicative of its concentration or dosage.

In operation, each time a pharmacist, a pharmacy technician or an automated pill dispensing machine fills a prescription vial, the vial is presented to a spectroscopic sensor system such as illustrated in FIG. 3 for verification of the contents of the vial. The sensor excites the Raman-active modes in the pharmaceutical 308 contained in the vial with laser diode 307 through the side, the top, or the bottom of the vial. The scattered Raman photons 304 are detected and the Raman spectral signature of the pharmaceutical in the vial is recorded.

This signature is compared to spectra stored in database 303 using a classification algorithm. Preferably, database 303 contains spectra of all pharmaceuticals that are likely to be dispensed at the pharmacy. As is known in the industry, one or more of several classification algorithms can be used to match the measured Raman spectrum to one of the spectra in database 303. Such classification algorithms include a correlation search, a first derivative search or a cluster analysis search. Other classification algorithms that can be used include: k-nearest neighbor, random forest, support vector machines, and soft independent modeling of class analogies. Correlation search and first derivative search type algorithms have been implemented in several commercially available software packages. For example, one commercially available software package for performing such analysis in the OMNIC software suite that is available from the Thermo Electron Corporation. The identity of the pharmaceutical in the vial is thus determined as being the identity of the pharmaceutical whose spectrum stored in the database best matches the measured Raman spectrum. Optionally, computer 305 may also calculate a confidence level (or other estimate) corresponding to the match. Based on the match, computer 305 then displays to the pharmacist or pharmacy technician its identification of the pharmaceuticals. In an optional embodiment, if the prescription vial already has a barcode, sample handling system 108 may read the barcode and then either validate that the pharmaceutical in the vial corresponds to the pharmaceutical identified by the barcode (as described below), or notify the pharmacist or pharmacy technician that the two identifications do not match. Mismatches can indicate, among other things, incorrect pharmaceuticals are the presence of counterfeit pharmaceuticals. Counterfeit pharmaceuticals are, for example, pharmaceuticals that have a similar appearance to the pharmaceutical identified by the barcode, but have different spectra.

Optionally, the sample handling system 108 may automatically sort the prescription vials into two different bins, one bin for all the vials containing the correct pharmaceuticals and the other bin for the vials containing the incorrect pharmaceuticals. The pharmacist can then double-check the vials in the "incorrect" bin. System 108 may also put a green sticker on the prescription vial to indicate that it has been verified by the system.

When the prescription vial contains a bar code identifying the pharmaceutical, the system can start the process by reading the bar code, then select the spectrum in its database corresponding to that pharmaceutical, compare the selected spectrum to the measured spectrum, and report whether the two spectra match or do not match. A better approach, which minimizes the possibility of false positives, is for the system to identify the pharmaceutical in the vial by comparing the spectrum from the pharmaceutical to the spectra in its database, and then display the identity on a display for the pharmacist, pharmacy technician or customer. Optionally, the identity of the pharmaceutical read from the barcode on the prescription vial is also displayed, so that the pharmacist, pharmacy technician and/or customer can verify that the two identities are indeed the same. This approach may still use the bar code identity to select the best parameters (e.g., scanning time, wavenumber range, etc.) for the Raman data collection.

Other spectroscopy techniques, such as NIR and FT-IR, can be used to obtain characteristic signature spectra of pharmaceuticals. Near-Infrared (NIR) spectroscopy works well for product analysis and quality control applications, but it suffers from lack of specificity compared to Raman spectroscopy and FT-IR absorption spectroscopy.

Raman spectroscopy also has some advantages compared to FT-IR spectroscopy. Some of these advantages are discussed in detail in an Application Note AN-9262 by Thermo Nicolet entitled, "The use of FT-Raman spectroscopy in the study of formulated pharmaceuticals," hereby incorporated by reference in its entirety. The application note discusses the collection of spectra from formulated pharmaceuticals.

Pharmaceutical samples generally give excellent Raman spectra, even when diluted with carriers. Commercial drugs are often used in small doses and compounded in an inert matrix that allows them to be packed into tablet form. This provides a slow, controlled release of the drug in the body. The intensity of Raman spectra obtained from different compounds can vary by a factor of 1000:1. This unique characteristic of Raman spectroscopy (e.g., in FT-IR, all compounds have a similar overall absorption) accounts for high-quality spectra recorded from drugs even in low concentrations. In general, the spectra generated by pharmaceutical compounds are stronger than those generated from carrier compounds.

In particular, Raman spectra are generally unaffected by highly polar bonds, such as C=O, O-H, C—Cl and amides, which produce very broad features in Fr-IR and obscure other useful information. The generally narrow, uncluttered bands of Raman spectroscopy make Raman spectra ideal for subtraction, quantitative analysis and library referencing.

Raman spectroscopy also has several practical advantages over FT-IR spectroscopy for the present application. Raman spectra can be recorded in the near-infrared region, where glass and plastic vials are transparent. Holders for Raman samples are readily available. In fact, many samples can be studied directly through their laboratory vials. This means that pharmaceutical tablets can be directly measured in the vials themselves.

Despite its advantages as an analysis tool for the present application, Raman spectroscopy has its own implementation challenges. For example, measurement intensity can be problematic. Only one out of a million incident photons is scattered as a Raman photon. Therefore it is very critical to design a Raman spectrometer which has very high throughput. Traditionally, this throughput problem has been solved with interferometric designs called FT-Raman. FT-Raman allows greater optical throughput than a conventional scanning/dispersive spectrometer, and it samples light more efficiently. FT-Raman with NIR excitation also avoids exciting fluorescence in almost all samples, making it a usable technique for general research and analysis, rather than for only a small number of spectra-emitting samples. However, FT-Raman is unsuitable for real time applications such as a high throughput screening system or a point of sale sensor system, both of which are critical to prescription verification system. Thus FT-Raman is not an optimal choice for the verification of pharmaceuticals in a retail pharmacy setting, because of the long spectral acquisition times required by FT-Raman.

With recent advances in CCD devices, a dispersive Raman instrument is a good alternative. However with conventional dispersive instruments, collecting the Raman scattered photons from a weak and diffuse source such as pharmaceutical tablet is extremely difficult. Dispersive instruments typically use an optical fiber-based input to gather light and disperse it onto the detector with a grating. In such a design, there is an inherent trade-off between resolution and throughput. While spectral resolution increases as slit width decreases, a narrow input slit greatly limits photon throughput and likewise measurement sensitivity.

A preferred embodiment of the present invention uses multimodal multiplex sampling (MMS) to obtain both high throughput and high specificity and sensitivity. MMS (described in U.S. patent application Ser. No. 10/417,066 (the "'066 application") and Ser. No. 11/334,546, both of which have been incorporated by reference herein in their entireties earlier) makes use of a coded aperture instead of a slit as the input aperture to sample nearly 1000 optical channels simultaneously into the system. With MMS, both resolution and etendue can be maintained and optimized in a single measurement. The layout of a typical MMS spectrometer is shown in FIG. 3. FIG. 3, as described above, is a schematic diagram of a multimodal multiplex sampling Raman spectroscopy system. This particular design uses a dispersive grating geometry with a coded aperture in place of a traditional slit/fiber. The coded aperture is designed to implement Hn, a full Hadamard matrix of order n, or an orthogonal column code. This spectrometer can simultaneously measure all the encodings in the matrix, eliminating the need for a dynamic system.

Figure 7:
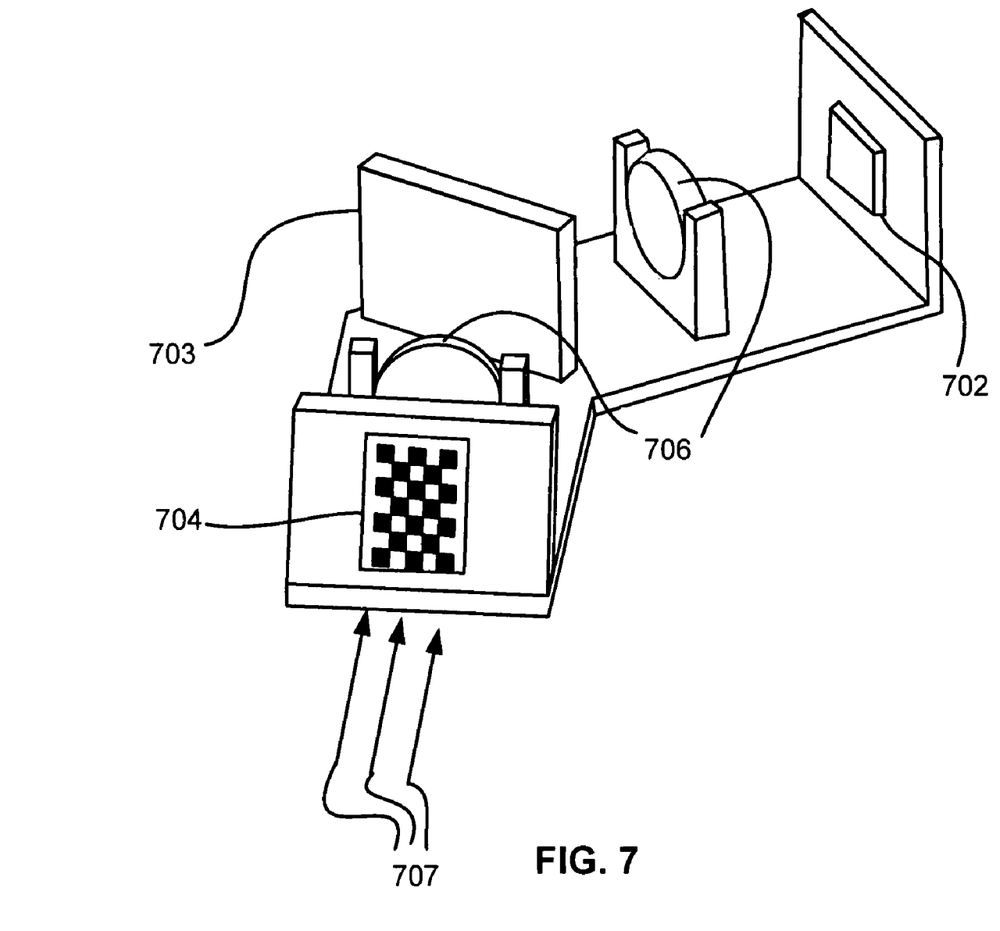
FIG. 7 is a schematic of an MMS-based Raman spectroscopic system for identifying pharmaceuticals according to an embodiment of the present invention.

FIG. 7 is a schematic of an MMS-based Raman spectroscopic system for identifying pharmaceuticals according to an embodiment of the present invention. As shown in FIG. 7, Raman photons 707 enter the system through coded aperture 704, and are collimated onto grating 703 by collimating lenses 706. The grating spectrally disperses the light, which is then imaged to a 2-D detector array 702, such as a CCD detector array. The CCD measures multiplexed patterns of the aperture depending on the spectral content of the source. The CCD measurements are then inverted by the use of appropriate algorithms and the source spectrum is reconstructed as explained in the '066 Application.

Figure 4A:
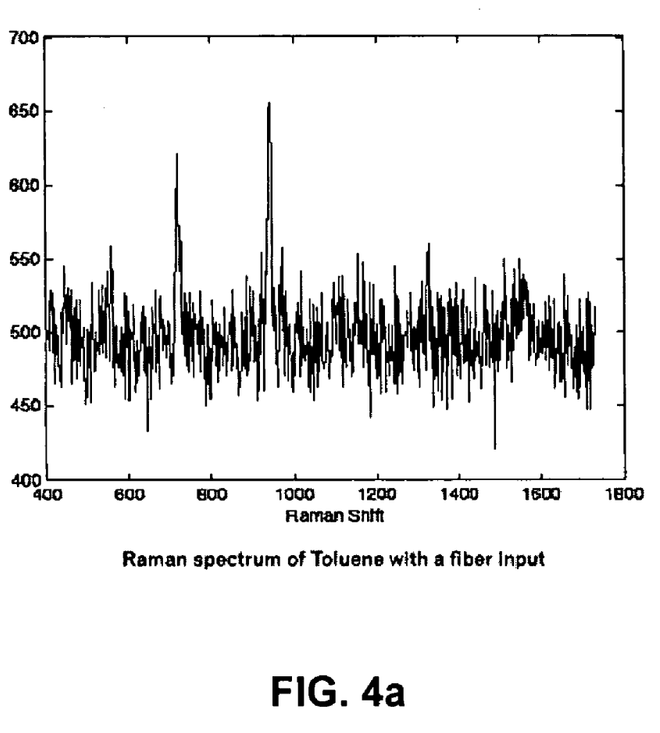
FIGS. 4a and 4b are exemplary Raman spectra of Toluene, obtained using conventional slit Raman spectroscopy (FIG. 4a) and multimodal Raman spectroscopy (FIG. 4b).
Figure 4B:
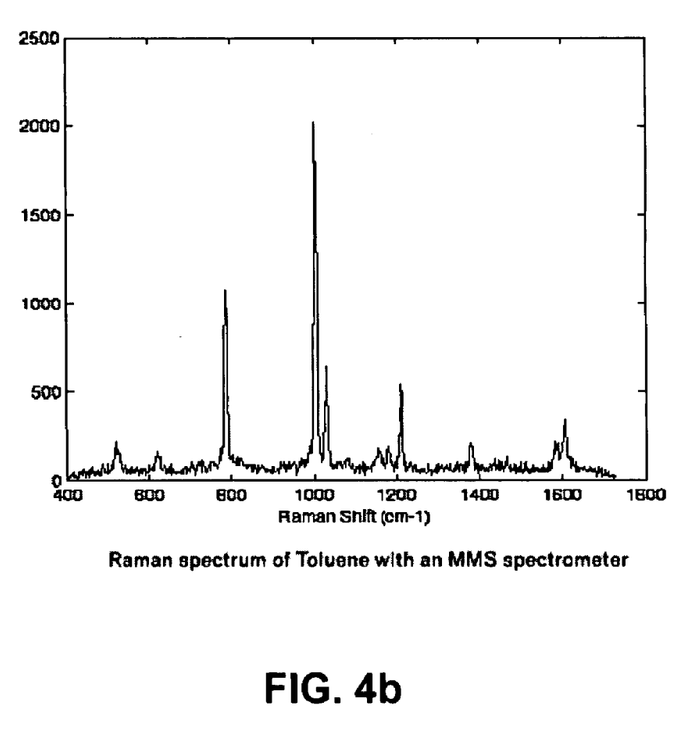

MMS spectrometers offer an enormous etendue advantage. MMS also offers a multiplex advantage which results in a substantial improvement in the signal to noise ratio performance. FIGS. 4a and 4b provide a comparison of the performance of a slit Raman spectrometer (FIG. 4a) with the performance of a Raman spectrometer using MMS technology (FIG. 4b).

This comparison of the known and commercially available spectroscopic measurement techniques shows that dispersive Raman spectroscopy using multimodal multiplexing Raman spectroscopy technology offers clear and compelling advantages over conventional "slit sampling" single mode spectrometers for measuring Raman spectra of pharmaceuticals through closed prescription vials.

Optionally, the laser beam (in Raman spectroscopy) can be coded to reduce the fluorescence background and thus improve the signal-to-noise ratio of the Raman spectrum. This is disclosed in U.S. Pat. No. 7,002,679, which is incorporated by reference herein in its entirety. Also, a 180 degree backscatter geometry may be implemented to minimize the signal generated through Raman scattering from the prescription vial.

Figure 5:
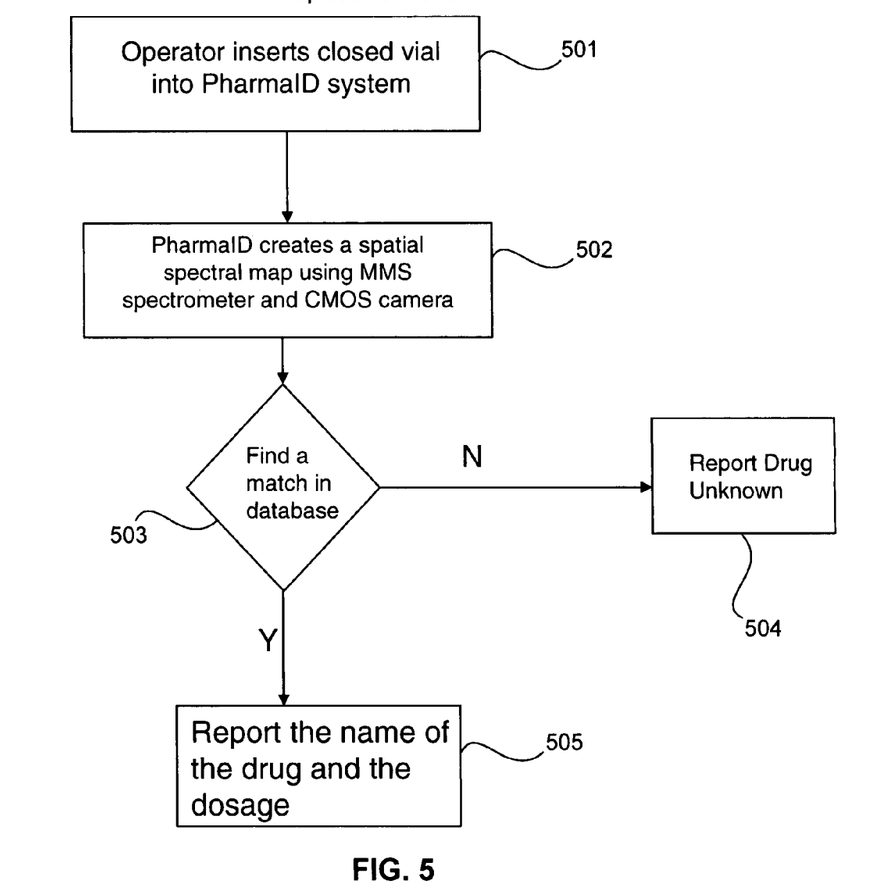
FIG. 5 is a flowchart of a method for identifying a pharmaceutical according to an embodiment of the present invention.

FIG. 5 is a flow chart for a method of identifying a pharmaceutical according to an embodiment of the present invention. In step 501, an operator initiates the pharmaceutical verification procedure by inserting a closed vial into sample handling system 108 (see FIG. 1). In step 502, spectroscopic sensor 110 obtains a spatial spectral map using an MMS spectrometer and a camera, such as a CMOS camera. In step 503, sample handling system 108 determines whether it has found a match in the database for the spectrum obtained in step 502. If a match is not found, in step 504, the system reports that a match has not been found. If a match is found, in step 505 the system reports the name of the pharmaceutical and, in a preferred embodiment, its dosage. Optionally, the system may also display a value indicating the confidence level of the match.

Optionally, if the prescription vial is not labeled with a bar code identifying the prescribed pharmaceutical, the system may print the identity of the pharmaceutical as determined in step 505 on a label, and that label is then attached (either by the pharmacist or the pharmacy technician or by the system itself) on the prescription vial.

Figure 6:
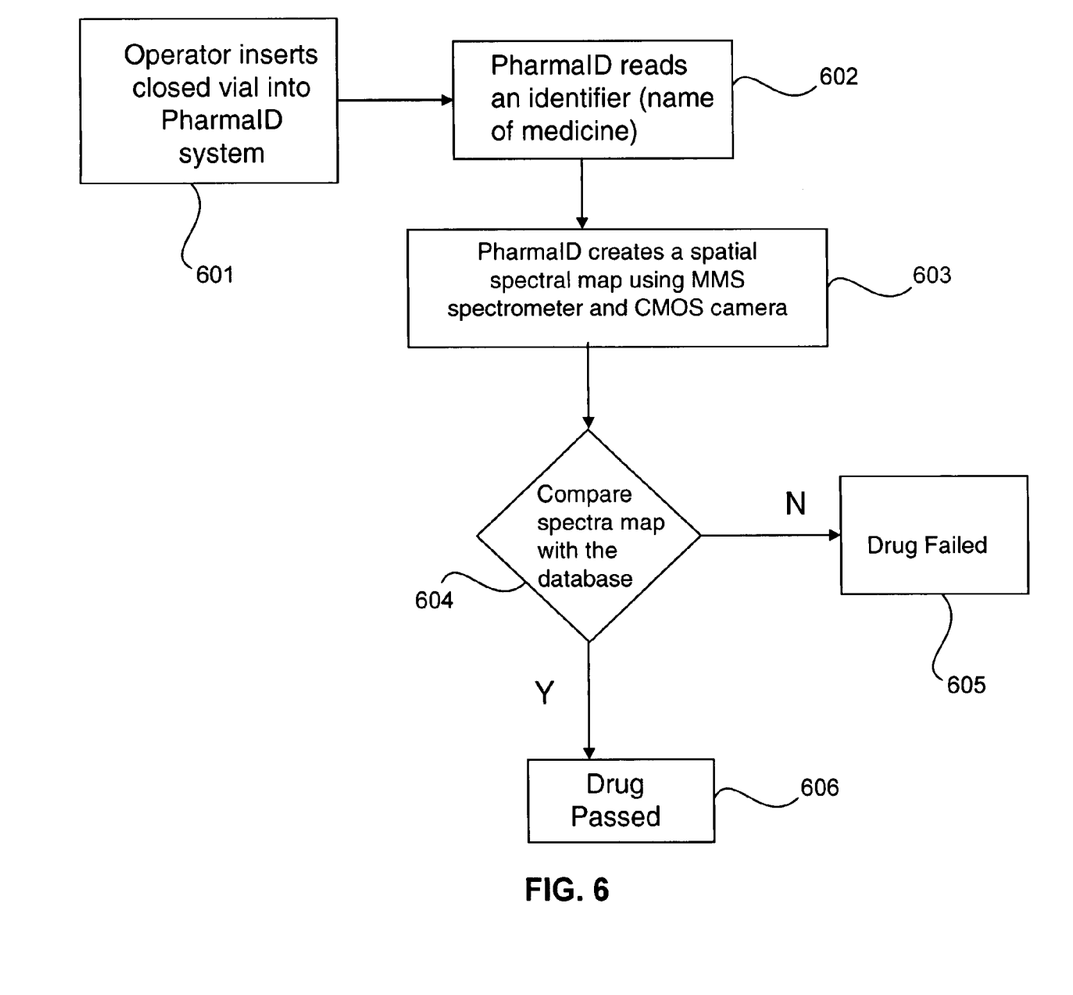
FIG. 6 is a flowchart of a method for identifying and verifying a pharmaceutical according to an embodiment of the present invention.

FIG. 6 is a flow chart for a method of identifying and verifying a pharmaceutical according to another embodiment of the present invention. In step 601, an operator initiates the pharmaceutical verification procedure by inserting a closed vial into the sample handling system 108 (see FIG. 1). In step 602, the system reads the barcode or other identifier on the closed vial. In step 603, spectroscopic sensor 110 obtains a spatial spectral map using an MMS spectrometer and a camera, such as a CMOS camera. In step 604, the system 108 identifies the pharmaceutical by comparing the spectral signature to the spectra in its database. If the system determines the pharmaceutical identified by the MMS spectrometer and the database does not match the identity of the pharmaceutical determined in step 602, the system reports that result in step 605. If the identity of the pharmaceutical identified by the MMS spectrometer and the database matches the identity of the pharmaceutical obtained in step 602, in step 606 the system reports that the pharmaceutical in the vial is indeed the prescribed pharmaceutical. Optionally, the system may also display a value indicating the confidence level of the match. Also optionally, sample handling system 108 may automatically sort the vials into a bin for correctly dispensed pharmaceuticals and a bin for incorrectly dispensed pharmaceuticals.

Figure 6A:
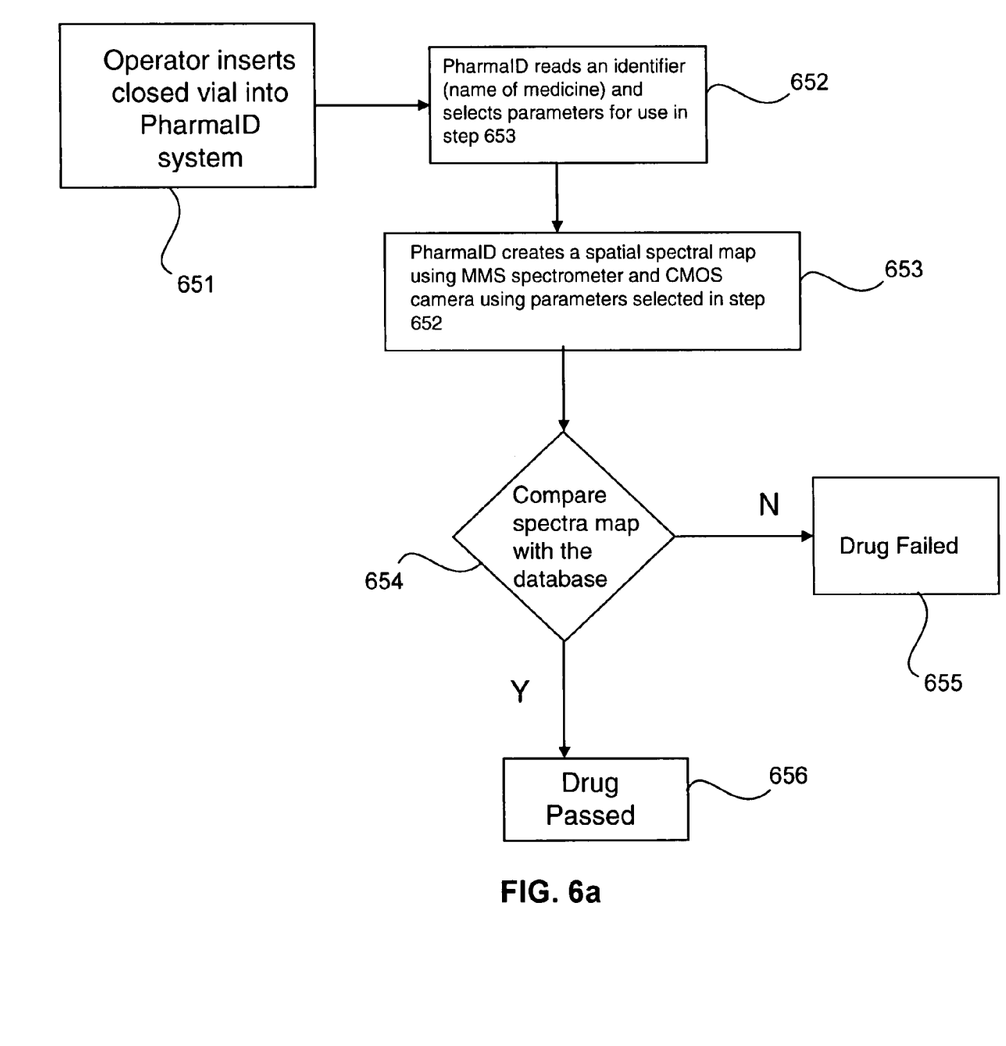
FIG. 6a is a flowchart of a method for identifying and verifying a pharmaceutical according to another embodiment of the present invention.

FIG. 6a is a flow chart for a method of identifying and verifying a pharmaceutical according to another embodiment of the present invention. Steps 651, 652, . . . , 656 are similar to steps 601, 602 . . . of FIG. 6. However, in step 652 the system, based on the identification of the pharmaceutical obtained from the bar code, selects the parameters for the most efficient and reliable collection of the Raman spectrum of the pharmaceutical in the vial. In step 653, the system uses those parameters to obtain the Raman spectrum of the pharmaceutical in the vial. In a further variation of this method, the system may determine that for certain pharmaceuticals (that have very distinctive and unique spectra and are never or very unlikely to produce false positives), it can take a shortcut by comparing the measured spectrum to the stored spectrum corresponding to the pharmaceutical identified by the bar code.

In either of the methods illustrated in FIGS. 5, 6, and 6a, the database may contain the weight of the pharmaceutical tablets, and may also contain the weight of the empty pharmaceutical vial. In a further preferred embodiment of the invention, the system may calculate the total weight of the vial and the pharmaceuticals to verify that the vial contains the correct number of pharmaceutical tablets.

Also, in either of the methods illustrated in FIGS. 5, 6, and 6a, the prescription vial may be mounted on a platform which rotates, to ensure that the laser beam illuminates a random selection of pharmaceutical tablets.

Algorithms for identifying an unknown compound by comparing spectra obtained from the unknown compound to spectra of known compounds stored in spectral libraries and for building spectral libraries are known in the art, as shown by, for example, the articles by P. C. Gillette, J. B. Lando and J. L. Koenig, "Computer-Assisted Spectral Identification of Unknown Mixtures," Applied Spectroscopy vol. 36, no. 6, 1982, 661–665; P. K. Aldridge et al., "Identification of Tablet Formulations Inside Blister Packages by Near-Infrared Spectroscopy," Applied Spectroscopy vol. 48, no. 10, 1994, 1272–76; M. J. Yang and P. W. Yang, "An IBM PC Based Computer Program for the Analysis of Infrared Spectra," Applied Spectroscopy, vol. 45, no. 10, 1991, 1739–45; and C. Gerhausser and K-A. Kovar, "Strategies for Constructing Near-Infrared Libraries for the Identification of Drugs Substances" (Applied Spectroscopy vol. 51, No. 10, 1997, 1504–06), which are all incorporated by reference herein.

Imaging device 107 (shown in FIG. 1) may also be used to assist in uniquely identifying the pharmaceutical in the prescription vial. Spectral and imaging database 102 may contain images of pharmaceuticals showing their size, shape, color and/or texture, or other data characterizing the size, shape, color and/or texture of known pharmaceuticals. For example, certain pharmaceutical tablets are provided in different sizes according to the dose of the pharmaceutical. In these cases, different doses of the same pharmaceutical may have the same spectral signature, such that the spectral signature cannot be used to identify the dosage in addition to identifying the pharmaceutical itself. Once the pharmaceutical has been identified, the imaging device can then be used to identify the dosage by comparing the size of the prescription tablet to the sizes for different dosages of that pharmaceutical in spectral and image database 102. Imaging device 107 can also be used to determine the shape and/or color of the tablets. This data can then be used as a double-check on the identity of the pharmaceutical, or to differentiate between different dosages or forms (tablets, caplets, liquids, pills, capsules, etc.) of the pharmaceuticals.

Algorithms for determining the size and/or shape of objects such as pharmaceuticals are well known in the art. For example, the article "Pattern Spectrum and Multiscale Shape Representation" by Petros Maragos (IEEE Transactions on Pattern Analysis and Machine Intelligence, Vol. 11, No. 7, July 1989), which is incorporated by reference herein, describes algorithms for determining the pattern spectrum of an image and quantifying various aspects of its shape/size content.

The present invention can be further enhanced by capturing a biometric identification (e.g., a fingerprint) or taking a photograph of the pharmacist or the pharmacy technician, so that the identity of the dispensing pharmacist or pharmacy technician may be determined if necessary for forensic purposes. Also, a voice recognition system may be used as a further check on the accuracy of the dispensed prescription, by having the operator announce the identity and/or number of tablets contained in the prescription vial, and the system validates that the prescription has be filled correctly. A credit card reader may also be integrated with the system, to identify the purchaser of the pharmaceutical as well as to process payments by credit cards.

The system of the present invention may be integrated with a central system (e.g., when the system is implemented for a chain of pharmacies) so that the database may be updated and supplemented from the central system, and/or so that the central system may keep track of the pharmaceuticals being dispensed (for inventory purposes and/or to make sure that an individual is not dispensed conflicting pharmaceuticals).

Depending upon the specific design of the system, a baffling and interlock system may be used with a Raman spectrometer to protect the operator from inadvertent exposure to the spectrometer's laser beam.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A method for identifying and verifying a phannaceutical in a prescription vial, comprising:
    storing a plurality of stored spectral signatures corresponding to known pharmaceuticals in a database;
    inserting the prescription vial containing the phannaceutical whose identity is to be verified into a sample handling system;
    measuring a spectral signature of the pharmaceutical whose identity is to be verified using a multimodal multiplex sampling (MMS) spectrometer;
    comparing the measured spectral signature to at least one of the stored spectral signatures;
    determining if the measured spectral signature matches one of the stored spectral signatures;
    if the measured spectral signature does not match one of the stored spectral signature, reporting that the identity of the pharmaceutical could not be determined; and
    if the measured spectral signature matches one of the stored spectral signatures, reporting the identity of the pharmaceutical.

2. The method of claim 1, further comprising sorting pharmaceuticals according to whether they have been identified or not been identified.

3. The method of claim 1, further comprising reading an identifier on the prescription vial to obtain a prescription identity and displaying the prescription identity on a display.

4. The method of claim 3, further comprising displaying the identity of the pharmaceutical on the display.

5. The method of claim 4, further comprising comparing the identity of the pharmaceutical to the prescription identity and determining whether the pharmaceutical identity matches the prescription identity.

6. The method of claim 1, further comprising reading an identifier on the prescription vial to obtain a prescription identity.

7. The method of claim 6, further comprising comparing the prescription identity to the pharmaceutical identity.

8. The method of claim 1, further comprising displaying a confidence level representing how well the measured spectral signature matched the stored spectral signatures.

9. The method of claim 1, wherein the multimodal multiplex sampling (MMS) spectrometer comprises a laser diode, and wherein the laser diode has a laser beam that is incident on the pharmaceutical after it is transmitted through the bottom, side or top of the prescription vial.

10. The method of claim 1, wherein the multimodal multiplex sampling (MMS) spectrometer is a Raman spectrometer.

11. A prescription verification system comprising:
    a database containing a plurality of spectral signatures corresponding to identified pharmaceuticals;
    a multimodal multiplex sampling (MMS) spectrometer;
    algorithms for matching spectra of pharmaceuticals to be verified obtaining using the MMS spectrometer to spectral signatures contained in the database corresponding to identified pharmaceuticals; and
    algorithms for identifying such pharmaceuticals to be verified.

12. The system of claim 11, wherein the MMS spectrometer is a Raman spectrometer.

13. The system of claim 11, further comprising a display for displaying the identity of the pharmaceutical to be verified.

14. The system of claim 11, wherein the pharmaceuticals to be verified are contained in a prescription vial, and wherein the prescription vial has a barcode label identifying the prescribed pharmaceutical,
    further comprising a barcode reader for reading the barcode label identifying the prescribed pharmaceutical.

15. The system of claim 14, further comprising a display for displaying the identity of the pharmaceutical to be verified and the identity of the prescribed pharmaceutical.

16. The system of claim 14, further comprising a pharmaceutical sorter for sorting pharmaceuticals to be verified into either one of a "match" bin or a "no match" bin.

17. The system of claim 11, further comprising an imaging device and an algorithm for processing images of the pharmaceuticals in the prescription vial to calculate parameters related to at least one of the size, shape, color and texture of the pharmaceuticals.

18. The system of claim 17, wherein the system uses the parameters related to at least one of the size, shape, color and texture of the pharmaceuticals to identify the pharmaceutical.

19. A method for identifying pharmaceuticals in a closed vial comprising:
maintaining a database of known spectral signatures corresponding to known pharmaceuticals:
placing the closed vial containing the pharmaceuticals in a spectrometer system;
directing a beam of electromagnetic radiation at the pharmaceuticals in the closed vial though the side, the bottom or the top of the closed vial;
measuring a spectral signature from the electromagnetic radiation reflected, transmitted or scattered by the pharmaceuticals in the closed vial;
matching the measured spectral signature to one of the known spectral signatures; and
reporting the identity of the pharmaceutical in the closed vial,
wherein the spectral signature is measured using multimodal multiplex sampling spectroscopy.

20. A method for identifying pharmaceuticals in a closed vial comprising:
maintaining a database of known spectral signatures corresponding to known pharmaceuticals;
placing the closed vial containing the pharmaceuticals in a spectrometer system;
directing a beam of electromagnetic radiation at the pharmaceuticals in the closed vial though the side, the bottom or the ton of the closed vial;
measuring a spectral signature from the electromagnetic radiation reflected, transmitted or scattered by the pharmaceuticals in the closed vial;
matching the measured spectral signature to one of the known spectral signatures; and
reporting the identity of the pharmaceutical in the closed vial,
wherein the spectral signature is obtained using multimodal multiplex sampling Raman spectroscopy.

21. The method of claim 20, wherein Raman photons are processed using a parallel optical channel processing system.

22. The method of claim 20, wherein the beam of electromagnetic radiation is a laser beam coded so as to reduce fluorescence background.

23. A method for identifying pharmaceuticals in a closed vial comprising;
maintaining a database of known spectral signatures corresponding to known pharmaceuticals;
placing the closed vial containing the pharmaceuticals in a spectrometer system;
directing a beam of electromagnetic radiation at the pharmaceuticals in the closed vial though the side, the bottom or the top of the closed vial;
measuring a spectral signature from the electromagnetic radiation reflected, transmitted or scattered by the pharmaceuticals in the closed vial;
matching the measured spectral signature to one of the known spectral signatures; and
reporting the identity of the pharmaceutical in the closed vial,
wherein the database also contains the weight of the known pharmaceuticals, further comprising calculating the total weight of the prescription vial and the pharmaceuticals, to verify that the vial contains the correct number of pharmaceuticals.

24. A method for identifying pharmaceuticals in a closed vial comprising:
maintaining a database of known spectral signatures corresponding to known pharmaceuticals;
placing the closed vial containing the pharmaceuticals in a spectrometer system;
directing a beam of electromagnetic radiation at the pharmaceuticals in the closed vial though the side, the bottom or the to of the closed vial;
measuring a spectral signature from the electromagnetic radiation reflected, transmitted or scattered by the pharmaceuticals in the closed vial;
matching the measured spectral signature to one of the known spectral signatures; and
reporting the identity of the pharmaceutical in the closed vial,
wherein the prescription vial is rotated to ensure that the beam of electromagnetic radiation illuminates a random selection of the pharmaceuticals in the closed vial.

25. A method for identifying an unknown pharmaceutical in a prescription vial comprising:
creating, naming, and storing a plurality of known pharmaceutical spectral signatures using one or more multimodal multiplex sampling (MMS) spectrometers;
measuring the spectral signature of an unknown pharmaceutical using a multimodal multiplex sampling (MMS) spectrometer;
comparing the measured spectral signature of the unknown pharmaceutical to at least one of the known spectral signatures;
determining if the measured spectral signature of the unknown pharmaceutical matches one of the known spectral signatures;
if the measured spectral signature of the unknown pharmaceutical does not match one of the known spectral signatures, reporting that the identity of the unknown pharmaceutical could not be determined; and
if the measured spectral signature of the unknown pharmaceutical matches one of the known spectral signatures, reporting the identity of the unknown pharmaceutical.

26. The method of claim 25, further comprising using a bar code reader to determine a prescribed identity of the unknown pharmaceutical.

27. The method of claim 26, further comprising verifying whether the identity of the unknown pharmaceutical, as determined from the comparison of the measured spectral signature to the known spectral signatures, matches its prescribed identity.

28. The method of claim 25, wherein the one or more multimodal multiplex sampling (MMS) spectrometer are Raman spectrometers.

29. The method of claim 25, wherein the measured spectral signature is obtained through a closed prescription vial.

* * * * *

UNITED STATES PATENT AND TRADEMARK OFFICE
CERTIFICATE OF CORRECTION

PATENT NO. : 7,218,395 B2
APPLICATION NO. : 11/454923
DATED : May 15, 2007
INVENTOR(S) : Stephen T. Kaye et al.

It is certified that error appears in the above-identified patent and that said Letters Patent is hereby corrected as shown below:

In the drawings, Sheet 5, FIG. 5, the text "Replacement Sheet" should be removed as shown in attached.

Column 7, line 51, the term "Fr-IR" should be replaced with the term --FT-IR--.

Column 11, lines 56-57, the term "phannaceutical" should be replaced with the term --pharmaceutical--.

Column 11, lines 60-61, the term "phannaceutical" should be replaced with the term --pharmaceutical--.

Signed and Sealed this

Twenty-fourth Day of June, 2008

JON W. DUDAS
*Director of the United States Patent and Trademark Office*

FIG. 5